(12) United States Patent
Brenner et al.

(10) Patent No.: US 9,149,271 B2
(45) Date of Patent: Oct. 6, 2015

(54) DEVICE AND METHOD FOR TREATMENT OF HEMORRHOIDS

(75) Inventors: Jacob S. Brenner, Menlo Park, CA (US); Gregory A. Magee, Menlo Park, CA (US); Angelo F. Szychowski, Mendocino, CA (US); Gaurav Krishnamurthy, Stanford, CA (US); Steven K. Jacobs, Pleasanton, CA (US)

(73) Assignee: THE BOARD OF TRUSTEES OF THE LELAND STANFORD, JR. UNIVERSITY, Palo Alto, CA (US)

( * ) Notice: Subject to any disclaimer, the term of this patent is extended or adjusted under 35 U.S.C. 154(b) by 1230 days.

(21) Appl. No.: 12/951,733

(22) Filed: Nov. 22, 2010

(65) Prior Publication Data
US 2012/0130403 A1 May 24, 2012

(51) Int. Cl.
*A61B 17/04* (2006.01)
*A61B 17/06* (2006.01)
*A61B 17/30* (2006.01)

(52) U.S. Cl.
CPC ......... *A61B 17/0482* (2013.01); *A61B 17/0469* (2013.01); *A61B 2017/06057* (2013.01); *A61B 2017/06176* (2013.01); *A61B 2017/306* (2013.01)

(58) Field of Classification Search
CPC ........... A61B 17/0469; A61B 17/0482; A61B 2017/306; A61B 2017/06176; A61B 2017/06057
See application file for complete search history.

(56) References Cited

U.S. PATENT DOCUMENTS

| 4,257,419 | A |   | 3/1981  | Goltner |
|-----------|---|---|---------|---------|
| 4,834,067 | A |   | 5/1989  | Block |
| 5,203,863 | A |   | 4/1993  | Bidoia |
| 5,395,033 | A | * | 3/1995  | Byrne et al. ............... 227/175.1 |
| 5,570,692 | A |   | 11/1996 | Morinaga |
| 5,741,273 | A |   | 4/1998  | O'Regan |
| 5,839,639 | A |   | 11/1998 | Sauer |
| 5,931,855 | A | * | 8/1999  | Buncke ......................... 606/228 |
| 6,083,241 | A | * | 7/2000  | Longo et al. .................. 606/219 |
| 6,102,271 | A |   | 8/2000  | Longo |
| 6,206,842 | B1|   | 3/2001  | Tu et al. |
| 6,234,955 | B1|   | 5/2001  | Silverman |

(Continued)

OTHER PUBLICATIONS

Eu, KW. "Stapled haemorrhoidectomy or Longo's procedure? Two totally different concepts", *Singapore Med J*, 2005, 46(10) p. 566-567.

(Continued)

*Primary Examiner* — Elizabeth Houston
*Assistant Examiner* — Son Dang
(74) *Attorney, Agent, or Firm* — William A. English; Vista IP Law Group LLP

(57) ABSTRACT

A device and method for treatment of hemorrhoids, in which the devices includes: a housing insertable into the rectum; a tissue port configured to receive a tissue segment containing at least a portion of a hemorrhoidal blood vessel; opposing needle chambers including at least one pair of corresponding needles coupled by a suture in which the pair of corresponding needles are substantially opposite to one another and in an active position substantially aligned with the tissue segment; a needle driver that advances the pair of corresponding needles through the tissue segment to encircle a portion of the hemorrhoidal blood vessel with the suture, thereby ligating the hemorrhoidal blood vessel; and an actuator coupled to at least one of the needle chambers that actuates the needle chambers such that another pair of corresponding needles is in the active position.

21 Claims, 9 Drawing Sheets

(56) References Cited

U.S. PATENT DOCUMENTS

| | | |
|---|---|---|
| 6,358,197 B1 | 3/2002 | Silverman |
| 6,506,157 B1 | 1/2003 | Teigman |
| 6,530,878 B2 | 3/2003 | Silverman |
| 6,638,286 B1* | 10/2003 | Burbank et al. ............. 606/157 |
| 6,695,764 B2 | 2/2004 | Silverman |
| 6,936,005 B2 | 8/2005 | Poff et al. |
| 6,989,016 B2 | 1/2006 | Tallarida |
| 7,037,314 B2 | 5/2006 | Armstrong |
| 7,118,528 B1 | 10/2006 | Piskun |
| 7,168,604 B2 | 1/2007 | Milliman |
| 7,220,266 B2 | 5/2007 | Gambale |
| 7,232,446 B1 | 6/2007 | Farris |
| 7,249,601 B2 | 7/2007 | Silverman |
| 7,399,304 B2* | 7/2008 | Gambale et al. ............. 606/139 |
| 7,399,305 B2* | 7/2008 | Csiky et al. ................. 606/139 |
| 7,402,320 B2 | 7/2008 | Mirizzi |
| 7,704,261 B2* | 4/2010 | Sakamoto et al. ............ 606/139 |
| 2003/0065336 A1* | 4/2003 | Xiao ............................ 606/144 |
| 2003/0183671 A1* | 10/2003 | Mooradian et al. ........ 227/175.1 |
| 2003/0236535 A1* | 12/2003 | Onuki et al. ................. 606/144 |
| 2004/0217146 A1* | 11/2004 | Beck .......................... 227/176.1 |
| 2005/0277945 A1 | 12/2005 | Saadat et al. |
| 2006/0167473 A1 | 7/2006 | Sheyer |
| 2006/0253126 A1* | 11/2006 | Bjerken et al. ................ 606/139 |
| 2006/0259041 A1 | 11/2006 | Hoffman et al. |
| 2006/0264706 A1 | 11/2006 | Piskun |
| 2007/0023475 A1 | 2/2007 | Csiky |
| 2007/0078486 A1 | 4/2007 | Milliman |
| 2008/0058786 A1 | 3/2008 | Boyden et al. |
| 2008/0249544 A1* | 10/2008 | Brand ........................... 606/144 |
| 2008/0281267 A1 | 11/2008 | Mehier |
| 2008/0287967 A1* | 11/2008 | Andreas et al. ............... 606/144 |
| 2010/0023023 A1* | 1/2010 | Popovic et al. ............... 606/142 |
| 2010/0160934 A1* | 6/2010 | Kelleher et al. .............. 606/139 |
| 2010/0331623 A1* | 12/2010 | Sauer et al. ................... 600/106 |
| 2011/0178536 A1* | 7/2011 | Kostrzewski ................. 606/144 |

OTHER PUBLICATIONS

Papagrigoriadis, A. "Stapled Anopexy with Doubled Stapling: a Safe and Efficient Treatment for Fourth Degree Haemorrhoids", *Acta chir belg*, 2006, 106, pp. 717-718.

* cited by examiner

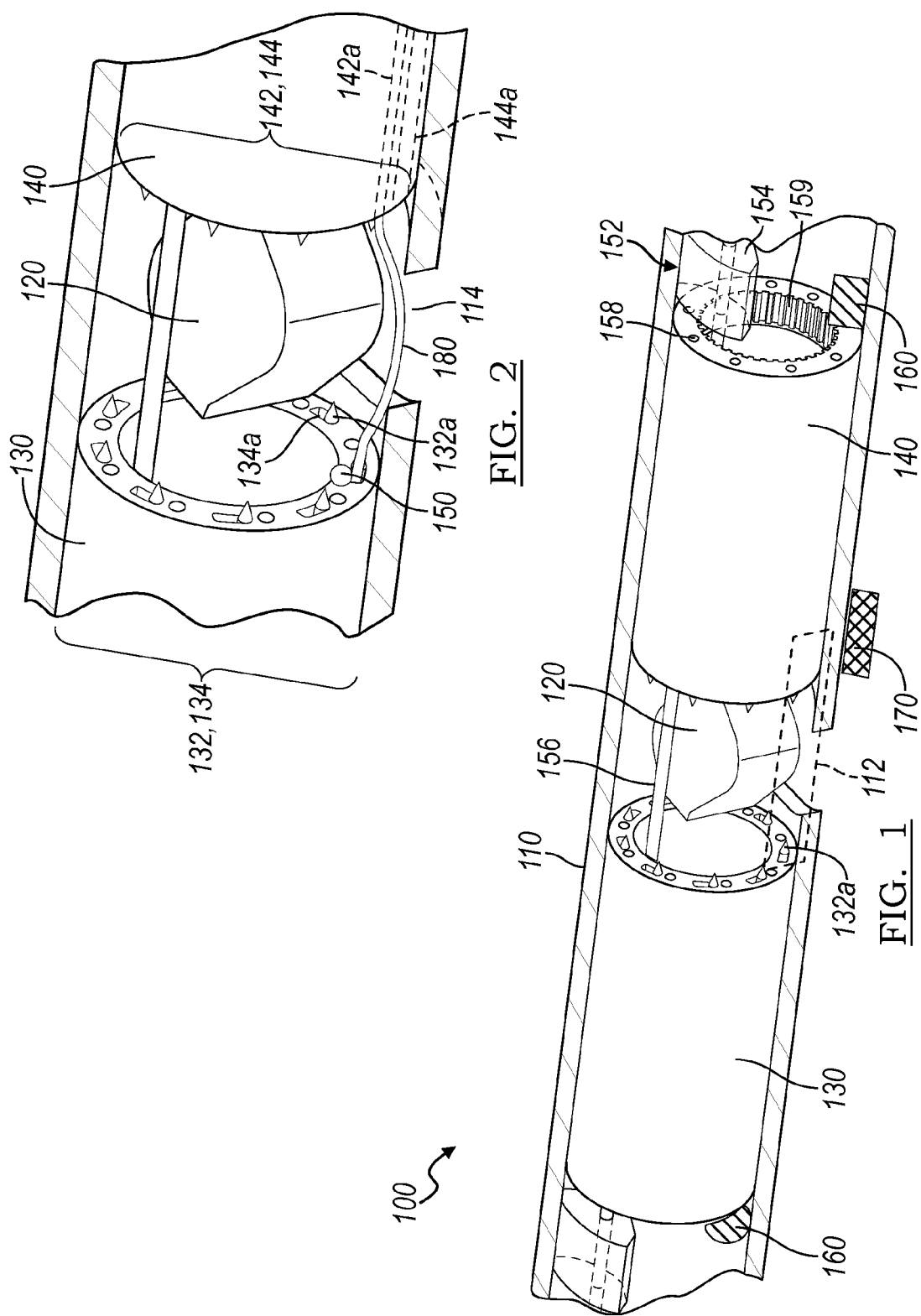

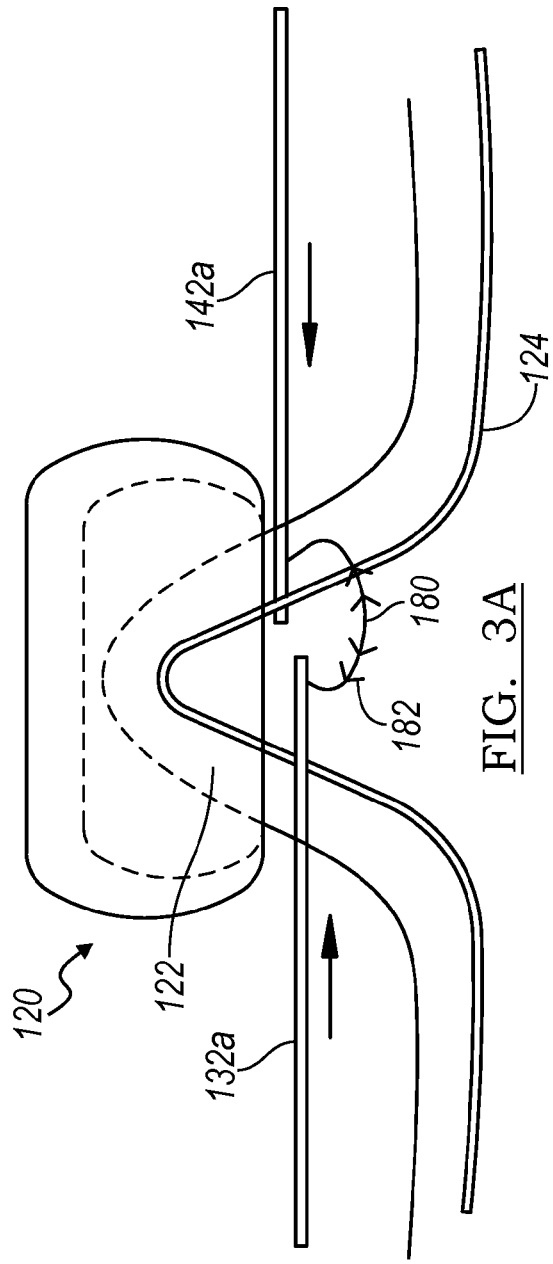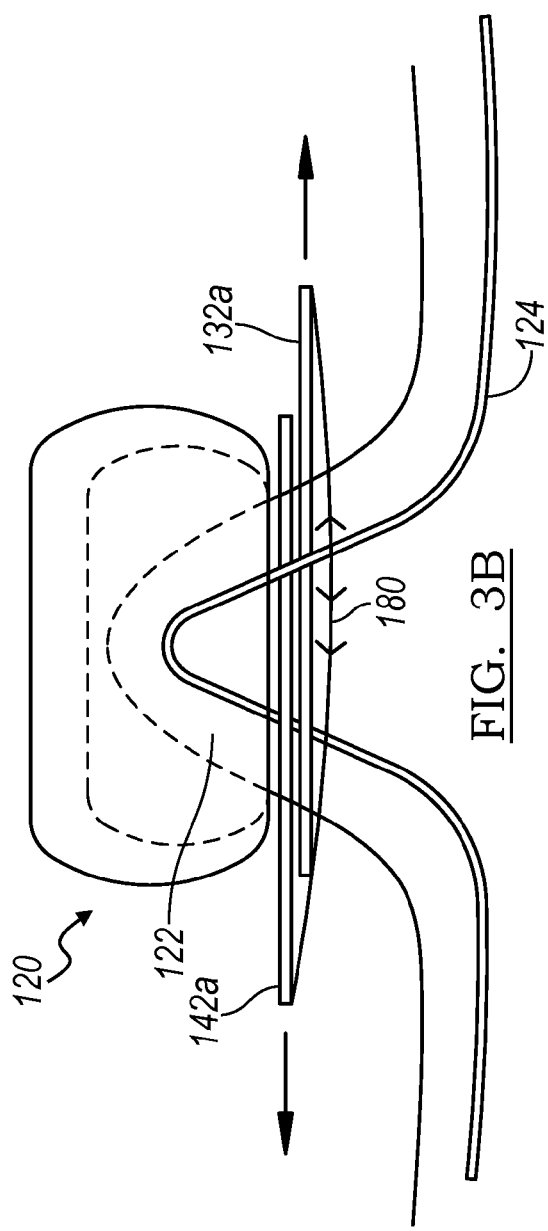

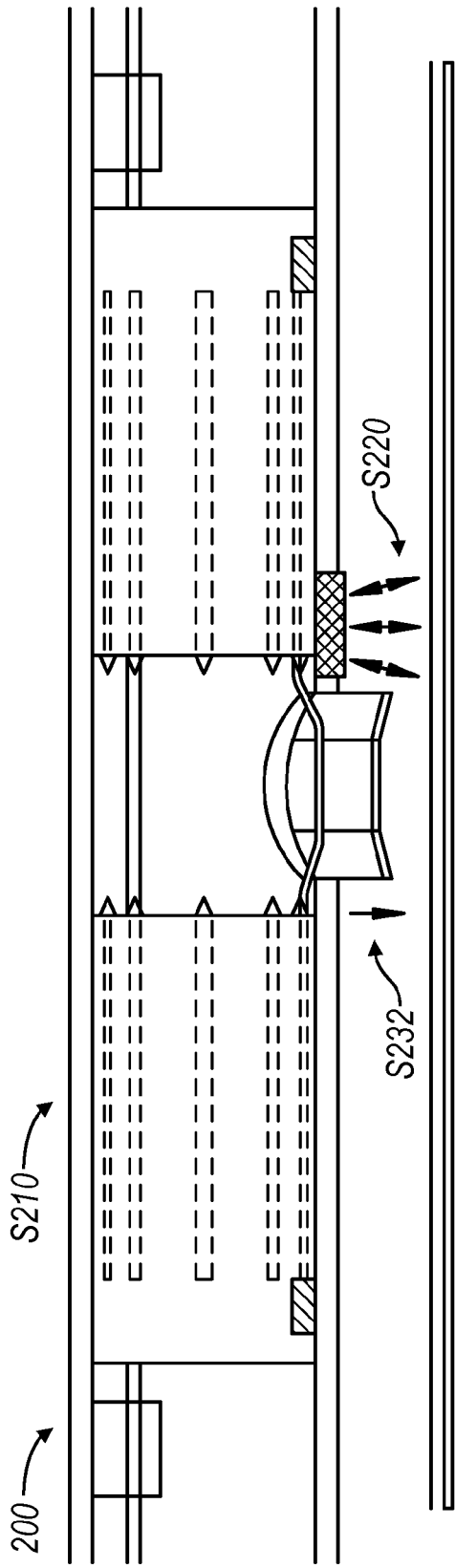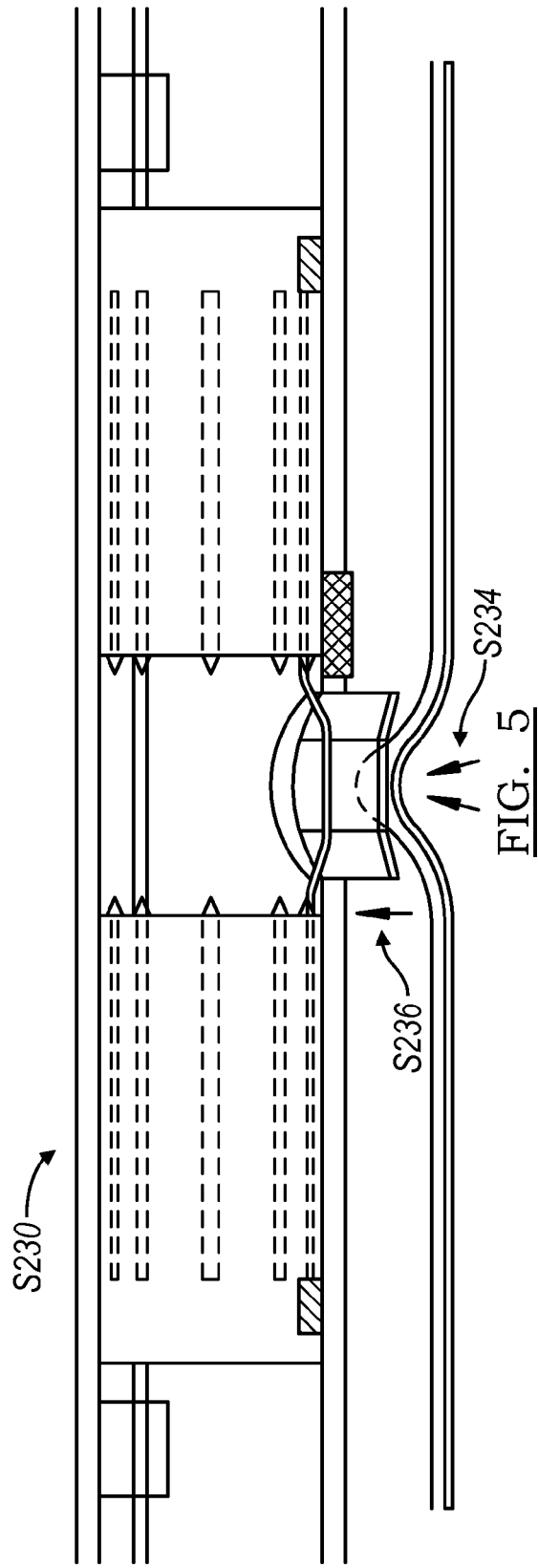

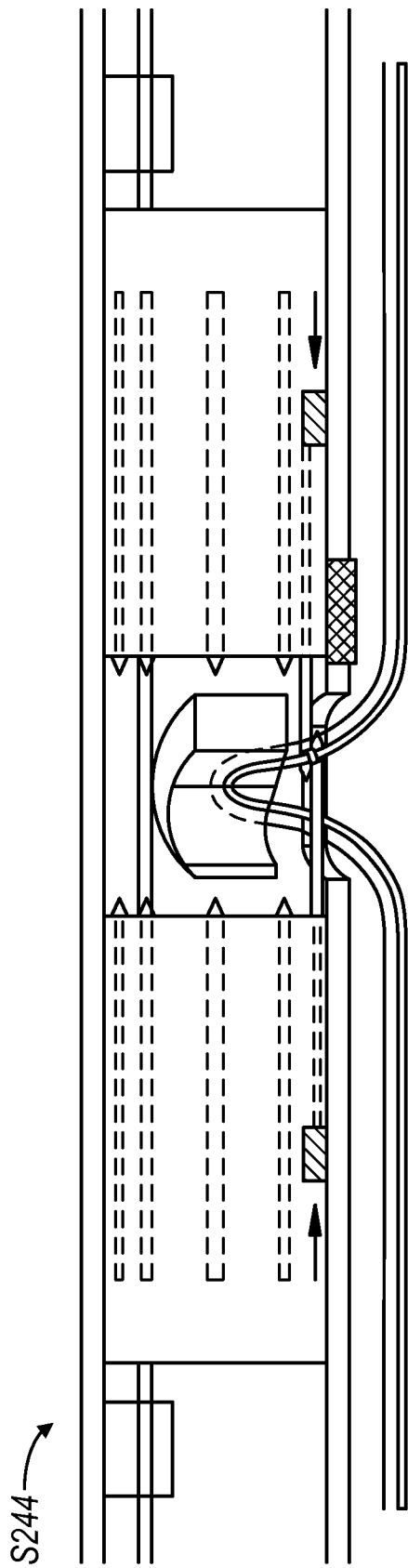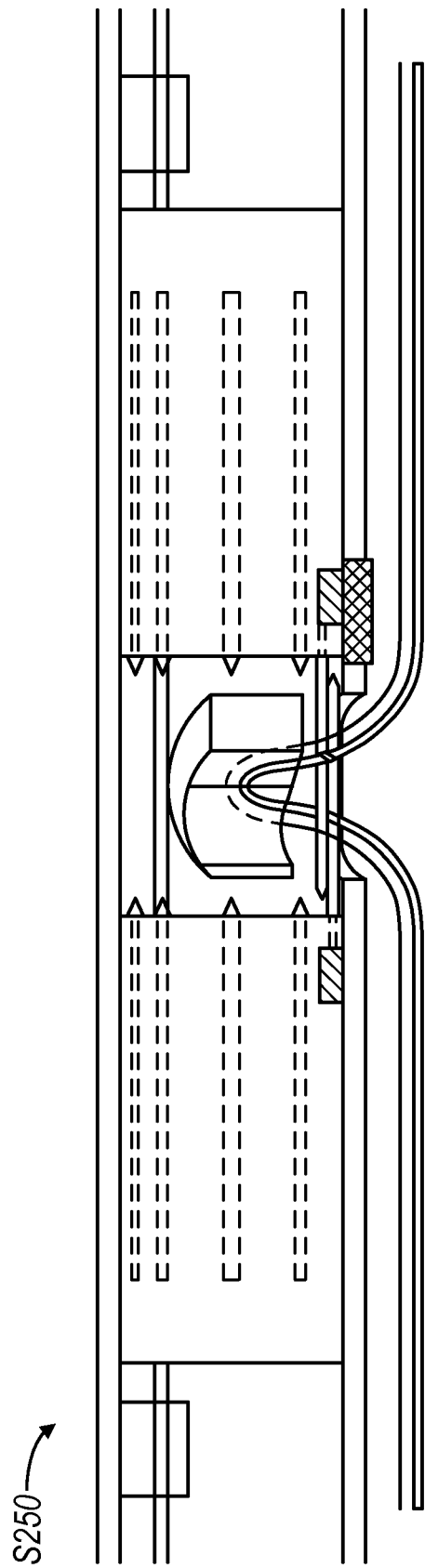

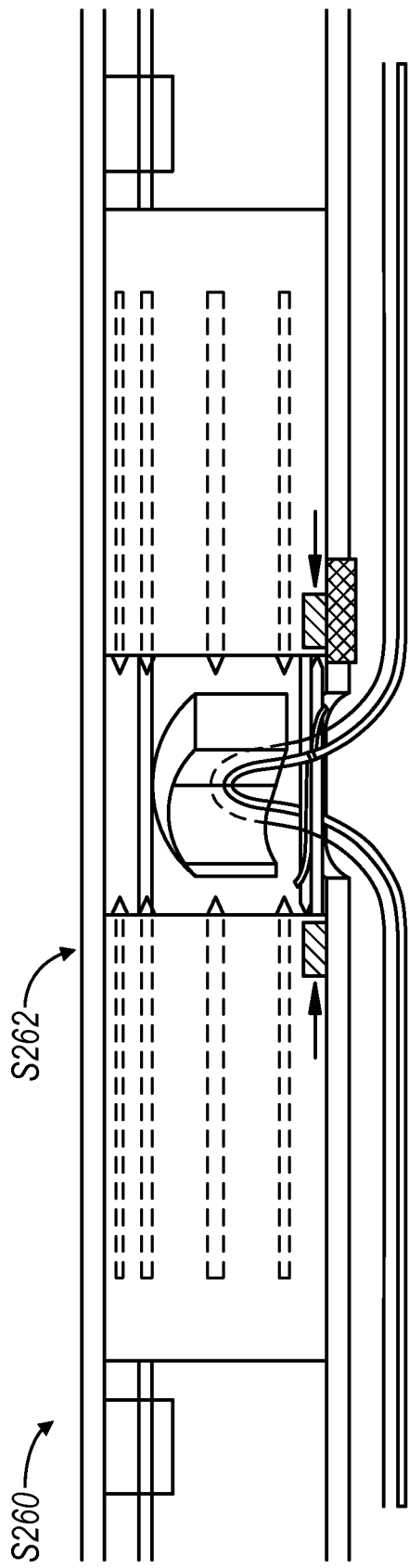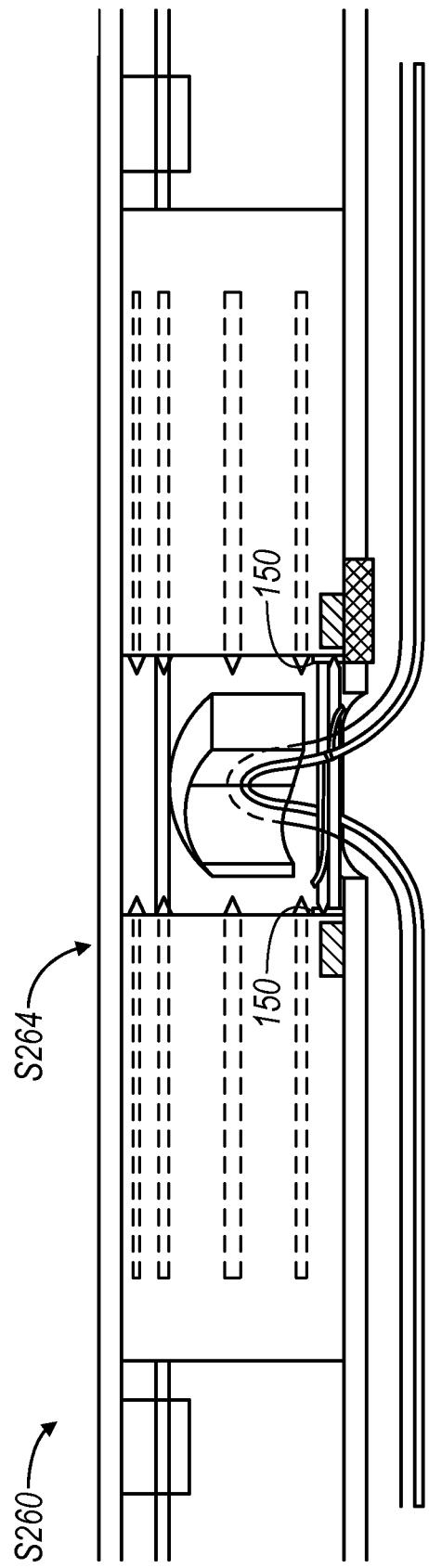

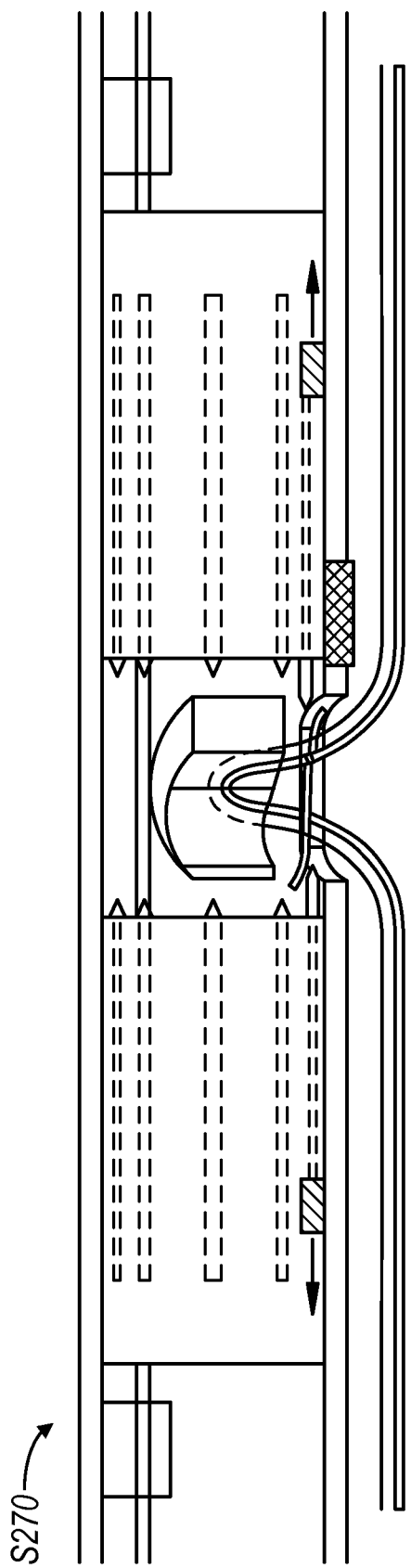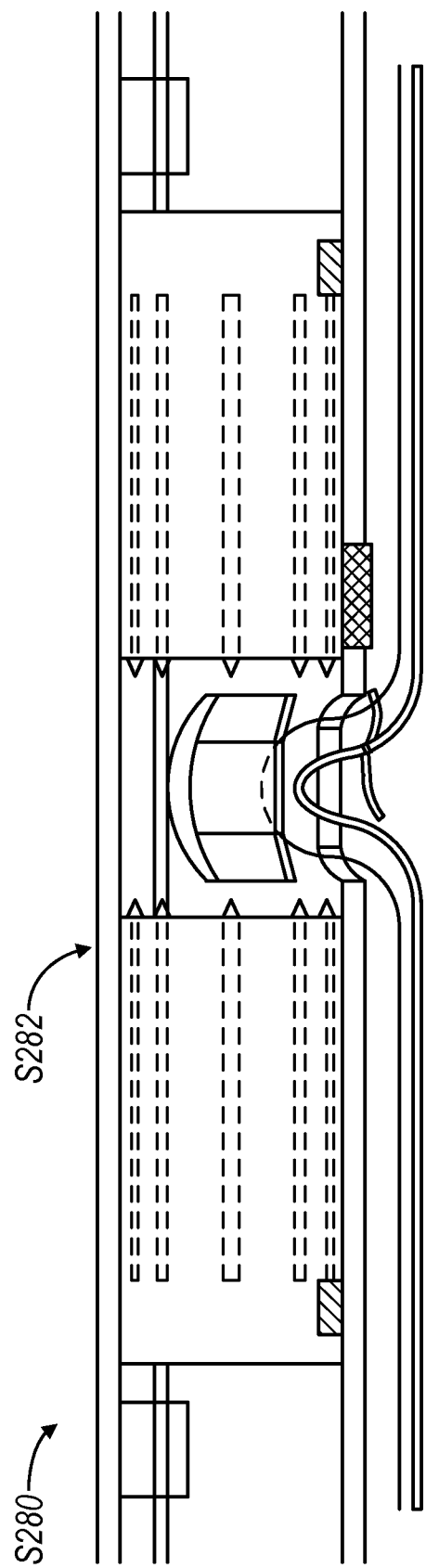

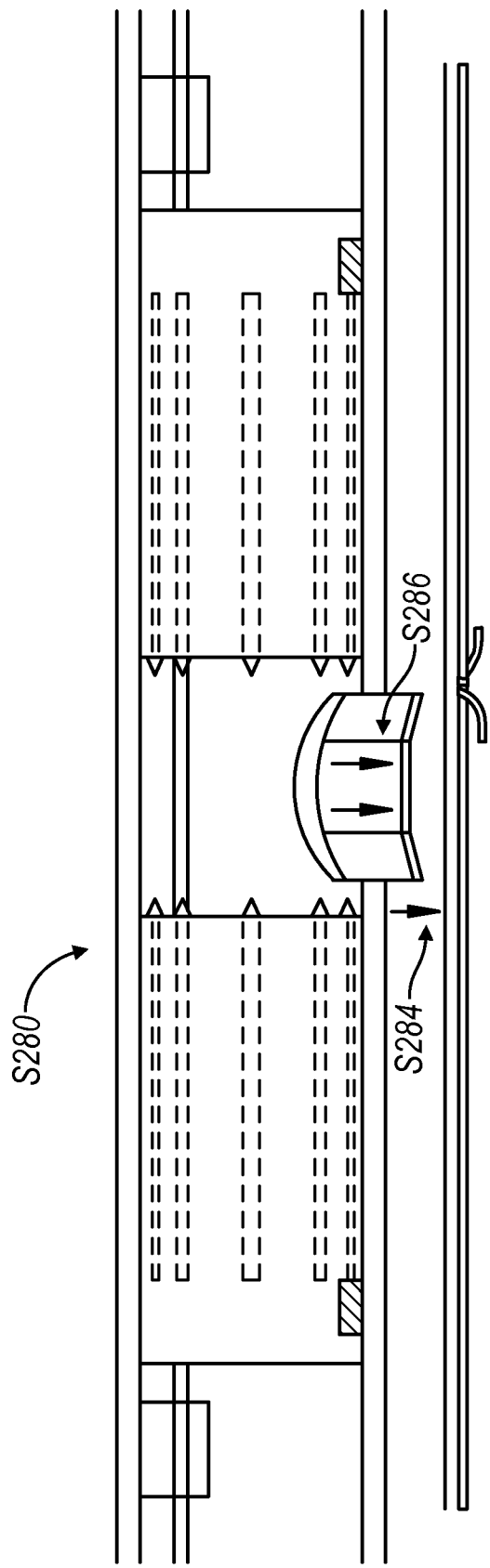

DEVICE AND METHOD FOR TREATMENT OF HEMORRHOIDS

TECHNICAL FIELD

This invention relates generally to the medical field, and more specifically to an improved device and method for treating hemorrhoids in the medical field.

BACKGROUND

Hemorrhoids are vascular structures in the lower portion of the rectum that may become painful and swollen. There are numerous home treatments (e.g., creams, diet changes, etc.) that may be used to treat hemorrhoids, but surgical treatment is often considered to be the most effective, particularly for serious cases of hemorrhoids. One common surgical treatment is hemorrhoid ligation, in which a swollen hemorrhoid is tied off at its base with a band, clip, or other ligation device to cut off blood flow to the hemorrhoid, so that the hemorrhoid shrinks and/or falls off. However, such ligation treatments are typically inconvenient and are uncomfortable for the patient. Furthermore, the use of implants such as bands or clips can be cumbersome to use. Thus, there is a need in the medical field to create an improved device and method for treatment of hemorrhoids. This invention provides such an improved device and method for treatment of hemorrhoids.

BRIEF DESCRIPTION OF THE FIGURES

FIG. 1 is a perspective view of the device of a preferred embodiment for treatment of hemorrhoids;

FIG. 2 is a perspective detailed view of FIG. 1;

FIGS. 3A and 3B are detailed schematic views of the blood vessel ligation process using a device of the preferred embodiment; and FIGS. 4-14 are schematic views of the various steps in the method of a preferred embodiment for treatment of hemorrhoids.

DESCRIPTION OF THE PREFERRED EMBODIMENTS

Figure 6:
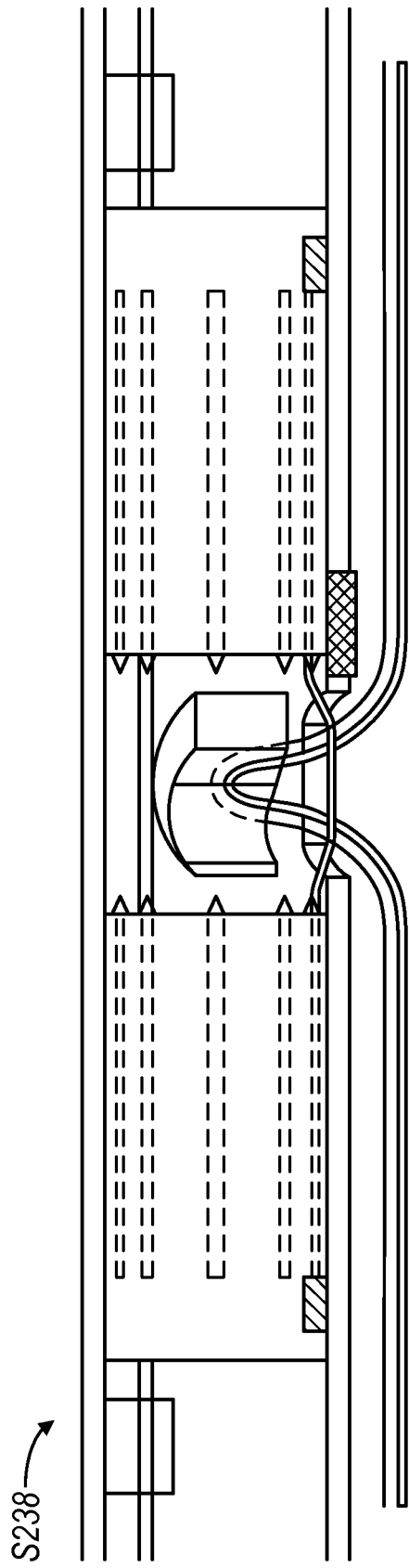

The following description of preferred embodiments of the invention is not intended to limit the invention to these preferred embodiments, but rather to enable any person skilled in the art to make and use this invention.

Device for Treatment of Hemorrhoids

As shown in FIGS. 1 and 2, the device 100 of a preferred embodiment for treatment of hemorrhoids includes: a housing 110 insertable into the rectum; a tissue port 120 coupled to the housing 110 and configured to receive a tissue segment 122 containing at least a portion of a hemorrhoidal blood vessel; a first needle chamber 130 disposed inside the housing no on a proximal side of the tissue port 120 and including a first needle 132a; a second needle chamber 140 disposed in the housing no on a distal side of the tissue port 120 and including a second needle 142a corresponding to the first needle, in which the first and second needles 132a and 142a are coupled by a suture 180; and a needle driver that advances the first and second needles through the tissue segment 122. The first and second needles may be substantially opposite to one another and in an active position 112 substantially aligned with the tissue segment 122, such that when the needle driver advances the needles through the tissue segment, the suture encircles a portion of the hemorrhoidal blood vessel, thereby ligating the hemorrhoidal blood vessel. In some embodiments, the first and second needle chambers may each include a plurality of needles to form multiple pairs of corresponding needles and the device may further includes an rotating drive 152 that actuates the needle chambers 130 and 140 such that another pair of corresponding needles is in the active position 112. The device 100 is preferably used to ligate a hemorrhoidal blood vessel in the treatment of hemorrhoids, but may alternatively be used to directly ligate a hemorrhoid, or any suitable segment of tissue for any suitable purpose. Ligation of the hemorrhoidal blood vessel (e.g., hemorrhoidal artery and/or hemorrhoidal vein) reduces blood flow to the hemorrhoid, thereby reducing the presence of and/or eliminating the hemorrhoid. The device may be sized with relatively small (e.g., narrow) dimensions, such that the procedure for treatment of hemorrhoids is minimally-invasive. Since the device preferably uses a bioresorbable suture, the use of the device to treat hemorrhoids preferably involves no implants that complicate the procedure and require retrieval post-procedure and/or post-recovery. Furthermore, in embodiments in which the needle chambers include a plurality of pairs of corresponding needles, the device may be used to ligate multiple hemorrhoidal blood vessels without requiring reloading and reinsertion of the device into the patient between successive ligations.

The housing 110 of the device functions to provide a body for conveying components of the device into the body of the patient. The housing no includes a cavity or other internal space within which various components of the device are located. The housing no is preferably adapted to be inserted into the rectum of the patient. For example, as shown in FIG. 1, the housing may be elongated and approximately cylindrical with a somewhat narrow diameter for entry through the anus. The housing no may alternatively be any suitable shape. The housing 110 is preferably a substantially closed structure, with smooth faces and edges such as for reduced tissue tearing upon insertion, but may alternatively have a number of apertures or other openings. The housing 110 may be long enough to extend into the rectum above the dentate line while maintaining some length outside of the body (e.g., to serve as a handle), and/or be coupled to a separate handle for operation and manipulation by a user. However, the housing may have any suitable dimensions and/or features.

The tissue port 120 functions to receive at least a portion of a tissue segment 122 and to restrain the tissue segment 122 during ligation of the hemorrhoidal blood vessel 124 with the suture. As shown in FIGS. 3A and 3B, the tissue port 120 preferably restrains at least a portion of the tissue segment 122 such that the pair of corresponding needles in the active position 112 is aligned with part of the tissue segment below the received portion of the tissue segment. Alternatively, the tissue port 120 may restrain the tissue segment 122 such that the pair of corresponding needles in the active position are aligned with the tissue port 120 and configured to pass through both the tissue port 120 and the tissue segment 122 during ligation, or the tissue port 120 may restrain the tissue segment in any suitable manner. The device 100 may include one or multiple tissue ports 120. The received tissue segment 122 preferably includes a hemorrhoidal artery, but may additionally and/or alternatively include a hemorrhoidal vein or other blood vessel. The tissue port 120 is preferably a suction port, coupled to a suction channel, that receives the tissue segment 122 through suction. For example, the suction channel may travel internally and/or externally along the housing 110 between a proximal end of the housing and the suction port, such that an external vacuum pump, syringe, or other means for providing suction force may be applied to the suction channel to draw tissue into the suction port. However, the tissue port 120 may receive the tissue segment 122 through any suitable means, such as pinching, hooking, or in cooperation with another device that pushes the tissue segment 122 into the tissue port. The tissue port 120 may be extendable outside of the housing 110, which may improve access to mucosal tissue for capture into the tissue port. The tissue port 120 may be retractable inside the housing 110, such as to allow alignment of the received tissue segment 122 with needles. For example, as shown in FIGS. 5 and 6, the tissue port 120 may include a capsule that passes back and forth through an aperture 114 in the housing 110 that allows access to tissue external to the housing 110. In operation, a vacuum pressure may be applied when the tissue port 120 is extended outside of the housing and adjacent to targeted tissue (e.g., adjacent to a hemorrhoidal artery or vein), and the tissue port 120 may then be retracted into the housing to contain the received tissue segment 122 within the housing. The tissue port may include open side walls or perforated walls, such as to allow the needles and suture access to the tissue within the tissue port.

The tissue port 120 may be rotatable to an angle that orients the hemorrhoidal blood vessel in the received tissue segment 122 preferably nonparallel to the housing 110, and more preferably nonparallel to at least one of the first and second needles. The tissue port 120 is preferably rotatable to expose the profile of the hemorrhoidal blood vessel to the needles, which may ease encircling the hemorrhoidal blood vessel with the suture. In one variation, the tissue port 120 is rotatable to an angle of approximately 45 degrees relative to at least one of the needles, which may have several advantages. First, the rotation results in less dimensional interference between the tissue port and other components. Second, ligation of rotated tissue involves less tissue deformation. Third, during ligation of rotated tissue, the tissue presents a thicker tissue cross-section to the needles and suture, which provides the suture more tissue to securely anchor in. In another variation, the tissue port 120 is rotatable to an angle of approximately 90 degrees relative to at least one of the needles. However, the tissue port may be rotated to any suitable angle during ligation. In an alternative embodiment, the tissue port may not be rotatable. In this alternative embodiment, the device may include curved needles that curve around the profile of the hemorrhoidal blood vessel as the needles are advanced, and/or the tissue port may be oriented relative to the needles in any suitable manner to facilitate encircling and ligation of the hemorrhoidal blood vessel with the suture.

The first and second needle chambers function to hold and/or direct the advancement of the needles. The first needle chamber 130 may be disposed inside the housing 110 on a proximal side of the tissue port 120, and the second needle chamber 140 may be disposed inside the housing 110 on a distal side of the tissue port 120. As shown in FIG. 2, both the first and second needle chambers preferably hold at least a first and a second needle, respectively, and more preferably a first plurality of needles 132 and a second plurality of needles 142, respectively. The first needle 132*a* in the first needle chamber 130 and the second needle 142*a* in the second needle chamber 140 are preferably coupled by at least one suture 180.

As shown in FIGS. 3A and 3B, the first and second needles are preferably substantially opposite to one another across the tissue port 120 and/or tissue segment 122 such that the first and second needles form a pair of corresponding needles. Similarly, in embodiments in which the needle chambers have a plurality of needles, each needle of the first plurality of needles 132 in the first needle chamber 130 is coupled to a corresponding needle of the second plurality of needles 142 in the second needle chamber 140 by a corresponding suture, and each pair of corresponding needles are substantially opposite to one another across the tissue port 120 and/or tissue segment 122 (or across the same general region of the housing). The needles 132 and 142 are preferably straight and aligned along a longitudinal axis of the device, but may alternatively be curved or shaped and/or oriented in any suitable manner. The needles may be made of metal or rigid plastic, or may additionally and/or alternatively include any suitable rigid or flexible material. The suture 180 coupling pairs of opposite, corresponding needles is preferably made of a bioresorbable material. The suture may include barbs 182 such as to retain traction and tension of the suture within the tissue segment, but may additionally and/or alternatively include other texturized features (e.g., bumps) to help retain the suture within the tissue segment. The suture may be coupled to the needle by tying the suture to the needle, with adhesive, and/or any suitable manner. The suture may be designed to couple between pairs of corresponding needles with a particular "breakaway" strength (that is lower than the tensile strength of the suture material), such that a particular tension within the needle/suture assembly will result in the suture decoupling from the needles. Advancement of the needles through the tissue segment 122 until the tension within the needle/suture assembly exceeds the "breakaway" strength (in other words, a suture release force) may be relied upon for decoupling the suture from the needles after ligation of the hemorrhoidal blood vessel.

The needle chambers 130 and 140 may each include at least one recess that receives a distal end of a needle from the opposite needle chamber. As shown in FIG. 2, the needles of each pair of corresponding needles may be slightly offset from one another. For example, the first needle chamber 130 may include a first recess 134*a* that receives a distal end of the second needle 142*a*, and the second needle chamber 140 may include a second recess 144*a* that receives a distal end of the first needle 132*a*. In a preferred embodiment, the first needle chamber 130 includes a first plurality of recesses 134 and the second needle chamber 140 includes a second plurality of recesses 144.

As shown in FIG. 2, each recess, or other suitable portion of the needle chamber, may be coupled to a cutter 150 that decouples the suture 180 from a received needle, preferably after the suture is sufficiently tightened around the hemorrhoidal blood vessel. The cutter 150 may be a blade or other sharp edge that shears the suture and/or a proximal end of the needle (for example, if the needle is bioresorbable). Alternatively, the cutter 150 may be separate from the recess, such as just in front of the entrance to the recess. In one variation, the cutter 150 is manually initiated and/or controlled. Furthermore, the cutter may be actuated through levers, gears, catches, a cam system, and/or any suitable mechanical and/or electrical coupling. The manual interface may include a first position corresponding to a "cutting" mode and a second position corresponding to a "noncutting" mode, such that the user may operate the manual interface to freely select between the cutting and noncutting modes. Alternatively, the cutter 150 may default to one of the modes and the manual interface may enable the user to temporarily transition the cutter to the other mode. For example, the cutter may default to a noncutting mode and the manual interface may enable the user to temporarily operate the cutter in the cutting mode. In another variation of the cutter, the cutter may be automatically initiated. For example, the insertion of the needle in the recess may trigger a blade or other suitable tool to cut across the entranceway to the recess and through the suture, thereby releasing the suture from the needle. Other suitable triggering and/or cutting mechanisms may be known to one ordinarily skilled in the art. The cutter may serve as a primary means for decoupling the suture from the needles, or may serve as a secondary means (e.g., for redundancy and safety reasons) after a primary means of advancing the needles until tension within the needle/suture assembly surpasses the "breakaway" strength, or suture release force.

As shown in FIG. 1, the needle chambers 130 and 140 may be coupled to a rotating drive 152, which rotates the needle chambers to orient a pair of corresponding needles into the active position 112. The rotating drive 152 preferably rotates the needle chambers about a longitudinal axis of the device to position a pair of corresponding needles into the active position 112, but may alternatively rotate the needle chambers in any suitable direction or manner. The rotating drive 152 preferably rotates the needle chambers after a pair of corresponding needles is spent (i.e., have been decoupled from their corresponding suture), to position another pair of corresponding needles in the active position 112 in preparation for another ligation. However, the rotating drive 152 may be used to rotate the needle chambers in any suitable manner, such as to position a particular selected pair of corresponding needles (e.g., a pair coupled to a longer or thicker suture suitable for a ligating larger tissue segment) in the active position 112. In one variation, the rotating drive may include one or more motors or any suitable actuator. For instance, at least one driving gear 158, mounted on a shaft 156 of an actuator 154, may engage internal teeth 159 of a needle chamber, such that rotation of the actuator shaft 156 causes rotation of the needle chamber. A second driving gear mounted on the actuator shaft may engage internal teeth of the other needle chamber, so that rotation of the actuator shaft simultaneously rotates both of the needle chambers in a synchronous manner, thereby preserving alignment of corresponding needle pairs. The rotating drive 152 may additionally and/or alternatively include a belt drive, a cable drive, chain and sprockets, or any suitable driving system to actuate the needle chambers in a synchronous or any suitable manner. Alternatively, the rotating drive 152 may include a second actuator and transmission system such that the needle chambers rotate independently of each other. In other words, each needle chamber may be coupled to its own respective actuator. The independent actuators may be synchronized in position by encoders. Furthermore, the rotating drive may include a clutch or other mechanical attachment that engages and disengages automatically (such as based on the current orientation of the needle chambers) and/or based on a manual control. However, the rotating drive may include any suitable transmission and/or actuating system.

In another variation, the rotating drive 152 may be actuated manually. For instance, the housing 110 may be coupled to a handle, such that the user may turn or otherwise manipulate the handle to rotate the needle chamber. Such a manual actuation may be accompanied by features indicating the degree of rotation (angular orientation of the needle chamber) and/or position of each pair of corresponding needles, such as detents, audible clicks, or reference marks on the housing 110, or any suitable visual, audio, and/or tactile indications.

In one preferred embodiment, the needle chambers 130 and 140 are cylindrical. In this embodiment, the needles and recesses are preferably distributed circumferentially around the perimeter of the needle chamber (preferably aligned along a longitudinal axis of the device, but may alternatively be oriented in any suitable direction). In one particular variation, as shown in FIG. 1, each needle chamber includes eight needles and eight recesses for receiving the distal ends of needles from the opposite needle chamber when the needles are advanced during ligation. The device may, however, include any suitable number of needle chambers, and each needle chamber may include any suitable number of needles. For example, each pair of corresponding needles may be in its own separate needle chamber.

The needle driver 160 functions to advance the needles through the tissue segment 122 in the tissue port 120, thereby encircling a portion of the hemorrhoidal blood vessel 124 with the suture 180 and ligating the hemorrhoidal blood vessel with the suture. The needle driver 160 may further function to withdraw the needles in the reverse direction, to withdraw the needles back into their original needle chambers after ligation of the hemorrhoidal blood vessel and decoupling of the suture from the needles are complete. As shown in FIGS. 3A and 3B, the needles are preferably advanced such that the needle tips are substantially on an opposite side of the hemorrhoidal blood vessel than the main length of the suture 180, such that the movement of the needles causes the suture 180 to form a loop around the profile of the hemorrhoidal blood vessel 124. The needle driver 160 may include a motor, a pneumatic system, a fluidic actuator, magnets, springs, or any suitable kind of actuator for advancing the needle. In one variation, the needle driver is mounted within or behind (with respect to the needles) the needle chamber, such as to drive the needles by pushing on the proximal end of the needle. In another variation, the needle driver 160 is mounted in front (with respect to the needles) of the needle chambers, such as to pull a needle from the opposite needle chamber through the tissue. For example, a magnetic or other attractive force may attract the distal end of the needle towards and through the tissue segment. Each of the first and second needle chambers 130 and 140 preferably has at least one needle driver 160. In a first variation, each needle chamber includes only one needle driver that is aligned with the active position 112 of the needles, such that the needle drivers are operatively coupled to only the particular pair of corresponding needles in the active position. In a second variation, each needle chamber includes a plurality of needle drivers, such that each needle of a needle chamber may be coupled to its own respective needle driver (that may operate only when its respective needle is in the active position). Alternatively, the device 100 may include one needle driver 160 coupled to both needle chambers using a suitable transmission for actuating both needle chambers with a single actuator. However, the device may include any suitable number of needle drivers.

In some embodiments, the device 100 further includes an ultrasound sensor 170 configured to detect blood flow of a hemorrhoidal blood vessel. The ultrasound sensor 170 is preferably a Doppler sensor, but may alternatively be any suitable kind of ultrasound sensor. The ultrasound sensor 170 is preferably coupled to the housing 110, adjacent to the tissue port and positioned along the longitudinal axis of the device such that when the ultrasound sensor is near a hemorrhoidal blood vessel, the tissue port 120 is in position to receive a tissue segment containing the hemorrhoidal blood vessel. However, the ultrasound sensor 170 may alternatively be positioned at any suitable location coupled to the housing. Furthermore, the device may include two or more ultrasound sensors. For example, the device may include two or more tissue ports, with each tissue port having its own respective ultrasound sensor.

In some embodiments, the device may further include one or more user interfaces coupled to an external portion of the device (such as a handle) that enables user control of one or more mechanisms of the device, including but not limited to: suction or other mechanisms for receiving tissue in the tissue port 120, extension and/or retraction of the tissue port 120 from the device, actuation of the needle driver 160, actuation of the cutter 150, retraction of the needles into the needle chambers 130 and 140, and actuation of the rotating drive 152 to rotate the needle chambers. In one variation, the user interface is a manual interface such as a mechanical trigger, a mechanical and/or electrical button or switch, a rotatable crank, a slidable shaft, a squeezable pneumatic pump, or any suitable manual interface that a user may engage in any suitable manner to selectively control one or more of the device mechanisms. In another variation, one or more of the device mechanisms is automatically initiated by some other action or mechanism. For example, the actuation of the cutter 150 may automatically trigger retraction of the needles into the needle chambers and/or actuation of the rotating drive 152. Furthermore, the various mechanisms of the device may be initiated or otherwise controlled through levers, gears, catches, a cam system, and/or any suitable mechanical and/or electrical coupling. Many suitable actuation systems are known to one skilled in the art. However, actuation of these mechanisms may include any suitable mechanical and/or electrical means.

In an alternative embodiment, the needle chambers 130 and 140 may be stationary and the tissue port may rotate within the housing 110 to align with a particular pair of corresponding needles. In other words, instead of different pairs of needles moving to an active position 112 having a fixed location, in the alternative embodiment the active position 112 may move to different pairs of needles having a fixed location. The mechanism for rotating the tissue port may be similar to the rotating drive 152 that rotates the needle chambers, or any suitable rotating mechanism.

Method for Treatment of Hemorrhoids

The method 200 of treatment of hemorrhoids preferably includes the steps of: Step S210, which includes providing a device including a housing, a tissue port, and opposing needle chambers including at least one pair of corresponding needles coupled by a suture; Step S230, which includes receiving at least a portion of a tissue segment in the tissue port in which the tissue segment includes at least a portion of a hemorrhoidal blood vessel; advancing the pair of corresponding needles toward each other S240; encircling a portion of the hemorrhoidal blood vessel with the suture S244, and tightening the suture S250, thereby ligating the hemorrhoidal blood vessel. The method may further include the steps of detecting a hemorrhoidal blood vessel in the tissue S220 with an ultrasound sensor before receiving a tissue segment in the tissue port. The method 200 may further include actuating the needle chambers S290 such that another pair of corresponding needles in the active position.

As shown in FIG. 4, the step of providing a device S210 preferably includes providing a device for treatment of hemorrhoids that is preferably similar to the device 100 described above, but may alternatively be any suitable device for treatment of hemorrhoids.

The step of receiving a tissue segment in the tissue port S230 functions to capture or fix the hemorrhoidal blood vessel in a known location relative to and accessible by the needles. As shown in FIG. 5, the step of receiving a tissue segment may include one or more of the steps of: extending the tissue port outside the housing S232, applying a suction force S234 to convey the tissue segment into the tissue port through suction, and retracting the tissue port within the housing S236 so that the tissue segment is substantially aligned with the pair of corresponding needles in the active position. However, the step of receiving a tissue segment in the tissue port S230 may include hooking the tissue segment into the tissue port, or any suitable step for conveying the tissue segment into the tissue port. The step of receiving a tissue segment preferably includes receiving at least a portion of a hemorrhoidal artery and/or vein, but may alternatively include any suitable kind of tissue.

As shown in FIG. 6, the step of receiving a tissue segment S230 may further include rotating the tissue segment S238 such that the hemorrhoidal blood vessel received in the tissue port is nonparallel to at least one of the pair of corresponding needles. The step of rotating the tissue segment S238 functions to expose the profile of the hemorrhoidal blood vessel to the needles and suture. The step of rotating the tissue segment S238 preferably includes rotating the tissue port, but may include inserting a spacer, block, or other object into the tissue port that reorients the tissue segment within the tissue port. The tissue segment is preferably rotated such that the hemorrhoidal blood vessel in the tissue port is approximately 45 degrees relative to at least one of the needles of the needle chambers.

Figure 7:
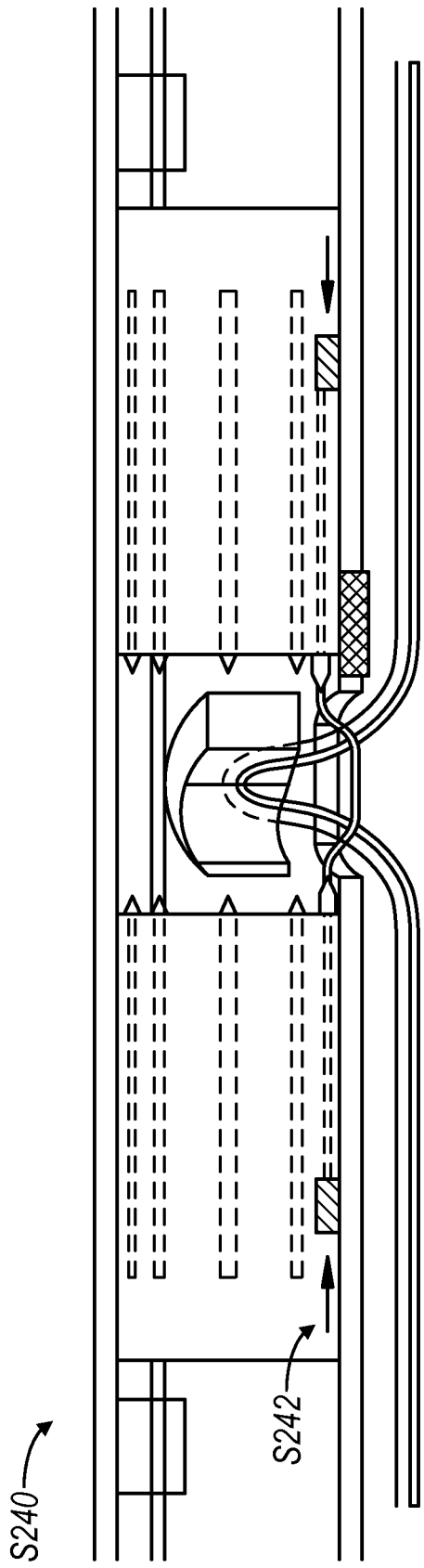

The step of advancing the pair of corresponding needles S240 preferably includes activating a needle driver S242 that drives the corresponding needles in the active position through the tissue segment, as shown in FIG. 7. During this step, other needles in the needle chambers are preferably located in inactive positions; that is, generally not in alignment with the tissue segment. The step of advancing the pair of corresponding needles S240 may include pushing a proximal end of the needles and/or pulling a distal end of the needles through the tissue segment. The needles are preferably advanced such that the needle tips are substantially on an opposite side of the hemorrhoidal blood vessel than the suture, but may be advanced in any suitable manner.

The step of encircling a portion of the hemorrhoidal blood vessel S244 functions to place the suture in an arrangement where the suture may ligate the hemorrhoidal blood vessel. As shown in FIG. 8, the relative positions of the needles, suture, and hemorrhoidal blood vessel in the tissue segment during the step of advancing the pair of corresponding needles toward each other preferably form a suture loop around the hemorrhoidal blood vessel.

The step of tightening the suture S250 functions to tie off the hemorrhoidal blood vessel with the suture. As shown in FIG. 9, the step of tightening the suture preferably includes further advancing the needles, at least until the ends of the suture are clear of the tissue segment (i.e., have passed into and completely out of the tissue segment in the tissue port). Barbs or other fixating features on the suture preferably retain the tension of the suture within the tissue segment, thereby maintaining the ligation of the hemorrhoidal blood vessel achieved in step S250.

As shown in FIG. 4, the method may further include the step of detecting a hemorrhoidal blood vessel in the tissue S220, preferably with an ultrasound sensor, preferably before the step of receiving a tissue segment in the tissue port. Alternatively, detecting a hemorrhoidal blood vessel S220 may be performed after the step of receiving a tissue segment in the tissue port, such as for verifying that the hemorrhoidal blood vessel is in the received tissue segment. The step of detecting a hemorrhoidal blood vessel S220 preferably includes detecting blood flow in a hemorrhoidal blood vessel with a Doppler sensor, but may additionally and/or alternatively include detecting blood flow in a hemorrhoidal blood vessel with any suitable sensor or any suitable means of detection.

The method 200 may further include a step for decoupling the suture from the advanced pair of corresponding needles S260. In a first variation, as shown in FIG. 10A, the method includes step S262, which includes the step of further advancing the needles until the tensile force applied to the suture exceeds a suture release force and allowing the suture to decouple from the needles. In this variation, the relative dimensions and arrangement of the suture, needles, and needle chamber may be designed to permit each of the further advanced needles to remain in the needle chamber opposite of their original needle chamber. In a second variation, as shown in FIG. 10B, the method includes deploying a cutter to decouple the suture from the needles after the step of tightening the suture. In a third variation, the method includes both steps S262 and S264 as redundant decoupling steps, to help ensure that the suture is decoupled from the needles after ligation. Further variations of the step may additionally and/or alternatively include any suitable means for decoupling the suture from the pair of corresponding needles.

As shown in FIG. 11, the method may further include a step of withdrawing the pair of corresponding needles S270 into their original needle chambers, after the suture is decoupled from the needles. However, the advanced needles may alternatively remain in the needle chamber opposite of their original needle chamber (which may involve withdrawing the needle driver back to their original needle chamber).

As shown in FIGS. 12 and 13, the method may further include the step of releasing the tissue segment from the tissue port S280. The step of releasing the tissue segment may include one or more of the following steps: unrotating the tissue segment S282 to restore the unrotated orientation of the hemorrhoidal blood vessel, extending the tissue port outside of the housing S284, and/or removing the suction force applied to the tissue port S286.

Figure 14A:
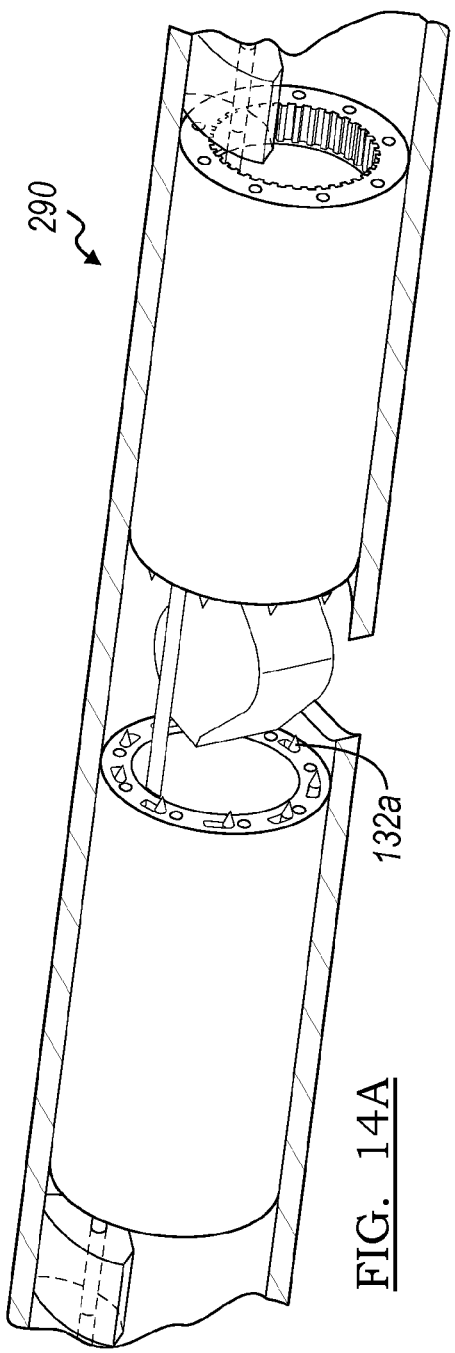
Figure 14B:
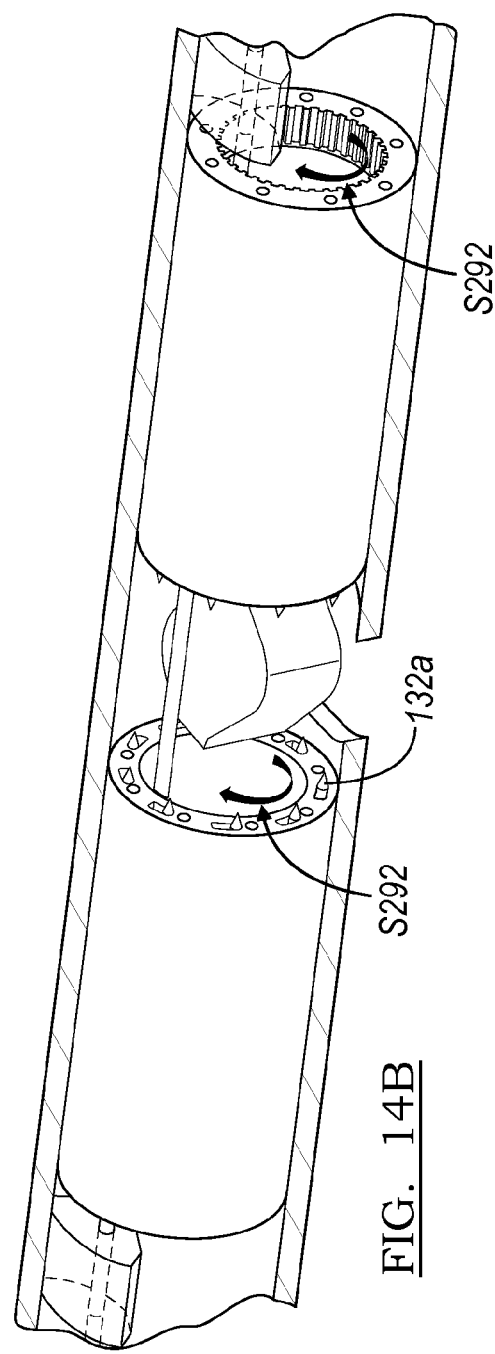

In embodiments in which each of the needle chambers includes a plurality of needles, the method may further include the step of actuating the opposite needle chambers S290 such that another pair of corresponding needles is moved to the active position. As shown in FIGS. 14A and 14B, the step of actuating the needle chambers preferably includes rotating the needle chambers about a longitudinal axis of the device S292, but may alternatively include any suitable actuation in any suitable direction.

As a person skilled in the art will recognize from the previous detailed description and from the figures and claims, modifications and changes can be made to the preferred embodiments of the invention without departing from the scope of this invention defined in the following claims.

We claim:

1. A device for treatment of hemorrhoids, comprising:
a housing;
a tissue port coupled to the housing and configured to receive a portion of a tissue segment containing at least a portion of a blood vessel;
an ultrasound sensor configured to detect blood flow of a blood vessel;
a first needle chamber disposed inside the housing on a proximal side of the tissue port and including a first needle;
a second needle chamber disposed in the housing on a distal side of the tissue port and including a second needle corresponding to the first needle, wherein the first and second needles are coupled by a suture, are substantially opposite to one another, and are in an active position substantially aligned with the tissue segment; and
a needle driver configured to advance the first and second needles through the tissue segment to encircle a portion of the blood vessel with the suture, thereby ligating the blood vessel,
wherein the first and second needles are in an offset alignment with each other.

2. The device of claim 1, wherein the tissue port includes a suction port configured to receive the tissue segment through suction.

3. The device of claim 1, wherein the first needle chamber includes a first recess that receives a distal end of the second needle, and wherein the second needle chamber includes a second recess that receives a distal end of the first needle.

4. The device of claim 1, wherein the first needle chamber is coupled to a first cutter that decouples the suture from the second needle, and the second needle chamber is coupled to a second cutter that decouples the suture from the first needle.

5. The device of claim 1, wherein the suture includes barbs.

6. The device of claim 1, wherein the suture is bioresorbable.

7. The device of claim 1, wherein the needle driver includes a first actuator coupled to the first needle and a second actuator coupled to the second needle, wherein the first and second actuators cooperate to advance the first and second needles toward each other.

8. The device of claim 1, wherein each of the first and second needle chambers includes a plurality of needles, wherein each needle of the first needle chamber is substantially opposite from a corresponding needle of the second needle chamber, and wherein the needles in each pair of corresponding needles are coupled by a corresponding suture.

9. The device of claim 8, further including an actuator coupled to at least one of the first and second needle chambers that actuates the first and second needle chambers such that another pair of corresponding needles is in the active position.

10. The device of claim 8, wherein the first and second needle chambers are cylindrical and each plurality of needles are distributed circumferentially around the needle chamber.

11. The device of claim 10, further including a rotating drive coupled to at least one of the first and second needle chambers, wherein the rotating drive rotates the first and second needle chambers about a longitudinal axis of the device such that another pair of corresponding needles is in the active position.

12. A device for treatment of hemorrhoids, comprising:
a housing;
a tissue port coupled to the housing and configured to receive a portion of a tissue segment containing at least a portion of a blood vessel;
a first needle chamber disposed inside the housing on a proximal side of the tissue port and including a first needle;
a second needle chamber disposed in the housing on a distal side of the tissue port and including a second needle corresponding to the first needle, wherein the first and second needles are coupled by a suture, are substantially opposite to one another, and are in an active position substantially aligned with the tissue segment and
a needle driver configured to advance the first and second needles through the tissue segment to encircle a portion of the blood vessel with the suture, thereby ligating the blood vessel,
wherein the tissue port is retractable inside of the housing.

13. The device of claim 12, wherein the tissue port is rotatable to an angle configured to orient the blood vessel nonparallel to at least one of the first and second needles.

14. The device of claim 13, wherein the tissue port rotates at least 45 degrees relative to at least one of the first and second needles.

15. A device for treatment of hemorrhoids, comprising:
a housing insertable into the rectum;
an ultrasound sensor coupled to the housing and configured to detect blood flow of a hemorrhoidal blood vessel;
a tissue port retractable into the housing and configured to receive at least a portion of a tissue segment containing at least a portion of a hemorrhoidal blood vessel;
a first cylindrical needle chamber disposed inside the housing on a proximal side of the tissue port and including a first plurality of needles distributed circumferentially around the first needle chamber; and
a second cylindrical needle chamber disposed in the housing on a distal side of the tissue port and including a second plurality of needles distributed circumferentially around the second needle chamber; wherein each needle of the first plurality of needles is substantially opposite from a corresponding needle of the second plurality of needles to form a plurality of pairs of corresponding needles, and wherein the needles in each pair of corresponding needles are coupled by a corresponding suture; wherein at least one pair of corresponding needles is configured to be in an active position substantially aligned with the tissue segment;
a needle driver configured to advance the pair of corresponding needles in the active position through the tissue segment to encircle a portion of the hemorrhoidal blood vessel with the suture, thereby ligating the hemorrhoidal blood vessel; and
a rotating drive coupled to at least one of the first and second needle chambers, wherein the rotating drive rotates the first and second needle chambers about a longitudinal axis of the device such that another pair of corresponding needles is in the active position.

16. The device of claim 15, wherein the tissue port includes a suction port configured to receive the tissue segment through suction.

17. The device of claim 16, wherein the tissue port is rotatable to an angle configured to orient the blood vessel nonparallel to at least one of the first and second needles.

18. The device of claim 15, wherein each needle of the first plurality of needles is in an offset alignment with a corresponding needle of the second plurality of needles.

19. The device of claim 18, wherein the first needle chamber includes a first set of recesses that receive distal ends of corresponding needles of the second plurality of needles, and wherein the second needle chamber includes a second set of recesses that receive distal ends of corresponding needles of the first plurality of needles.

20. The device of claim 15, wherein each suture includes barbs.

21. The device of claim 15, wherein each suture is bioresorbable.

* * * * *